United States Patent [19] [11] 4,122,194
Evans et al. [45] Oct. 24, 1978

[54] ARYL SULPHUR COMPOUNDS AS ANTIASTHMATICS

[75] Inventors: Delme Evans, Chalfont St. Peter; John Christopher Saunders, Maidenhead; William Robert Nigel Williamson, Slough, all of England

[73] Assignee: Lilly Industries Limited, London, England

[21] Appl. No.: 838,276

[22] Filed: Sep. 30, 1977

[30] Foreign Application Priority Data

Oct. 14, 1976 [GB] United Kingdom ............... 42683/76

[51] Int. Cl.² ............................................. A61K 31/10
[52] U.S. Cl. .............................. 424/337; 260/607 AR; 260/609 F
[58] Field of Search ................... 260/607 AR, 609 F; 424/337

[56] References Cited
U.S. PATENT DOCUMENTS 3,102,917  9/1963  Reifschneider ................. 260/609 F
3,188,352  6/1965  Reifschneider ................. 260/609 F

OTHER PUBLICATIONS

Chemical Abstracts, 43, 577c (1949), M. Protiva et al.
Chemical Abstracts, 44, 1685d (1950), C. Kroger.
Chemical Abstracts, 44, 5835b (1950), E. Amstutz et al.
J. Ind. Chem. Soc., 34, 581 (1957).
Derwent Abstract No. 46672w/28 of Japanese Patent J49116-229.

Primary Examiner—Lewis Gotts
Assistant Examiner—Molly C. Eakin
Attorney, Agent, or Firm—Kathleen R. S. Page; Arthur R. Whale

[57] ABSTRACT

An aryl sulphur compound of formula (I):

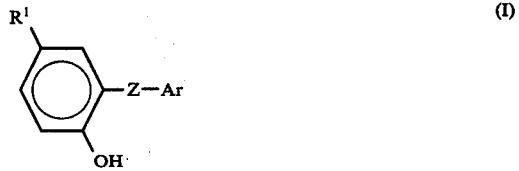

where $R^1$ is $C_{1-4}$ alkyl; Ar is a phenyl group optionally substituted by halogen or $C_{1-4}$ alkyl and wherein Z is S or SO, having antiallergy activity.

14 Claims, No Drawings

ARYL SULPHUR COMPOUNDS AS ANTIASTHMATICS

This invention relates to a class of novel aryl sulphur compounds, to methods of preparing such compounds, to pharmaceutical formulations and to methods of treating allergic conditions involving use of such compounds.

According to the present invention there is provided an aryl sulphur compound of formula (I):

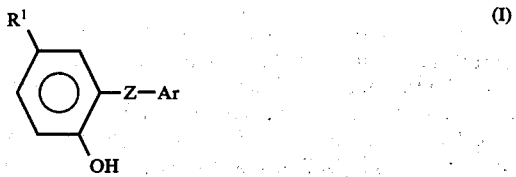

wherein $R^1$ is $C_{1-4}$ alkyl, Ar is a phenyl group optionally substituted by halogen or $C_{1-4}$ alkyl and wherein Z is S or SO, or a pharmaceutically-acceptable salt thereof.

Preferably $R^1$ is ethyl and/or Ar represents a phenyl group substituted with a para-substituent such as chlorine or methyl.

The invention also provides a pharmaceutical formulation which comprises a compound of formula (I), or a pharmaceutically-acceptable salt thereof, associated with a pharmaceutically acceptable carrier therefor.

The invention further provides a method of treating a mammal susceptible to an allergic condition, and particularly a method of treating immediate hypersensitivity diseases such as asthma, which comprises administering to the animal a therapeutically effective amount of a compound of formula (I) as defined above.

In a further aspect of the invention there is provided a method of making a compound of formula (I) as defined above, which method comprises reacting together a compound of formula:

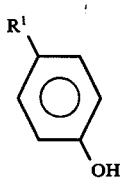

and a compound of formula:

ArSH in the presence of chlorine to give a compound of formula (I) in which Z is S; followed if desired, by oxidation to give a compound of formula (I) in which Z is SO.

Oxidation of a compound of formula (I) in which Z is S may advantageously be effected using hydrogen peroxide. Substantially equimolar quantities of the compound of formula (I) and hydrogen peroxide should be used.

Use of hydrogen peroxide in excess of two moles per mole of the compound of formula (I) in which Z is S should be avoided since this will lead to the formation of a compound of the type (I) in which Z is $SO_2$.

The aryl sulphur compounds of the present invention are useful in the prophylactic treatment of immediate hypersensitivity diseases including asthma and in the alleviation of *status asthmaticus* in humans. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointment, for example, containing from 1 to 10% by weight of the active compound in a suitable base, soft and hard gelatin capsules, suppositories, injection solutions and suspensions in physiologically acceptable media, and sterile packaged powers absorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I).

Dosages of from 0.5 to 100 mg/kg per day, preferably 2 to 20 mg/kg, of active ingredients may be administered. It will however readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The invention will be further illustrated by the following Examples:

EXAMPLE 1

4-Ethyl-2-(phenylthio) phenol

Chlorine gas was passed into a stirred, cooled (0° C.) solution of 4-ethylphenol (30.5g) and thiophenol (22g) in dichloromethane (100ml) for 3 hours. The solution was stirred overnight at room temperature the solvent was distilled off on a rotary evaporator and the residual oil was distilled, the product being in the higher boiling fraction (160°–180° C. at about 0.5 cm Hg). This fraction was chromatographed on a silica column, being eluted with hexane progressively enriched with chloroform to give the title compound (12.5g), as a clear liquid, $n_D^{23} = 1.6130$.

EXAMPLES 2 AND 3

There was also prepared by the method of Example 1 the following: 2-(4-Chlorophenylthio)-4-ethylphenol, $n_D^{22} = 1.6205$; and 4-Ethyl-2-(4-methylphenylthio)-phenol.

EXAMPLE 4

2-(4-Chlorophenylsulphinyl)-4-ethylphenol 2-(4-Chlorophenylthio)-4-ethylphenol (1.3g) was dissolved in glacial acetic acid (50 ml) and treated with aqueous hydrogen peroxide (0.57 ml 30% W/V). The mixture was kept under nitrogen and heated under reflux for 1 hour. On cooling, the solution was poured into water (400 ml) and a gummy solid separated out. This gummy solid was extracted with ethyl acetate and the organic fraction was washed with water, dried over magnesium sulphate and evaporated leaving a residual oil. The oil was dissolved in hot hexane, charcoaled, filtered and cooled, whereupon the title compound separated as a white crytstalline solid (0.7g) (mp 137° C.).

EXAMPLES 5 AND 6

There were prepared by the method of Example 4, the following: 4-Ethyl-2-(phenylsulphinyl)phenol, m.p. 145° C., and 4-Ethyl-2-(4-methylphenylsulphinyl)-phenol.

We claim:

1. A pharmaceutical formulation for the treatment of asthma comprising a compound of formula (I)

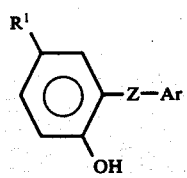

(I)

wherein $R^1$ is $C_{1-4}$ alkyl; Ar is a phenyl group optionally substituted by halogen or $C_{1-4}$ alkyl and Z is S or SO, or a pharmaceutically acceptable salt thereof, associated with a pharmaceutically acceptable carrier therefor.

2. A method of treating a mammal susceptible to asthma which comprises administering a therapeutically effective amount of a compound of formula (I),

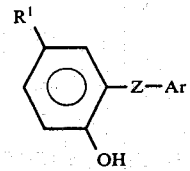

(I)

wherein $R^1$ is $C_{1-4}$ alkyl; Ar is a phenyl group optionally substituted by halogen or $C_{1-4}$ alkyl and Z is S or SO, or a pharmaceutically acceptable salt thereof, to the mammal.

3. The formulation of claim 1 in which the compound of formula (I) is 4-ethyl-2-(phenylthio)phenol.

4. The formulation of claim 1 in which the compound of formula (I) is 2-(4-chlorophenylthio)-4-ethylphenol.

5. The formulation of claim 1 in which the compound of formula (I) is 4-ethyl-2-(4-methylphenylthio)phenol.

6. The formulation of claim 1 in which the compound of formula (I) is 2-(4-chlorophenylsulphinyl)-4-ethylphenol.

7. The formulation of claim 1 in which the compound of formula (I) is 4-ethyl-2-(phenylsulphinyl)phenol.

8. The formulation of claim 1 in which the compound of formula (I) is 4-ethyl-2-(4-methylphenylsulphinyl)-phenol.

9. The method of claim 2 wherein the compound of formula (I) is 4-ethyl-2-(phenylthio)-phenol.

10. The method of claim 2 wherein the compound of formula (I) is 2-(4-chlorophenylthio)-4-ethylphenol.

11. The method of claim 2 wherein the compound of formula (I) is 4-ethyl-2-(4-methylphenylthio)phenol.

12. The method of claim 2 wherein the compound of formula (I) is 2-(4-chlorophenylsulphinyl)-4-ethyl-phenol.

13. The method of claim 2 wherein the compound of formula (I) is 4-ethyl-2-(phenylsulphinyl)phenol.

14. The method of claim 2 wherein the compound of formula (I) is 4-ethyl-2-(4-methylphenylsulphinyl)-phenol.

* * * * *